(12) United States Patent
Uchida

(10) Patent No.: US 7,153,266 B2
(45) Date of Patent: Dec. 26, 2006

(54) NONCONTACT TONOMETER

(75) Inventor: Koji Uchida, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 413 days.

(21) Appl. No.: 10/653,965

(22) Filed: Sep. 4, 2003

(65) Prior Publication Data

US 2004/0054277 A1    Mar. 18, 2004

(30) Foreign Application Priority Data

Sep. 17, 2002   (JP) ............................. 2002-270351

(51) Int. Cl.
*A61B 3/16* (2006.01)
(52) U.S. Cl. .................... 600/399; 600/398; 600/401
(58) Field of Classification Search ................ 600/398, 600/399, 400, 401, 402
See application file for complete search history.

(56) References Cited

U.S. PATENT DOCUMENTS

| | | | |
|---|---|---|---|
| 3,585,849 A | 6/1971 | Grolman ..................... 73/80 |
| 5,107,851 A | 4/1992 | Yano et al. ................. 128/648 |
| 5,183,044 A * | 2/1993 | Nishio et al. .............. 600/406 |
| 5,500,696 A | 3/1996 | Masuda et al. ............. 351/205 |
| 5,822,034 A | 10/1998 | Shimashita et al. ........ 351/212 |
| 6,053,867 A | 4/2000 | Iijima ....................... 600/399 |
| 6,120,444 A | 9/2000 | Miyakawa et al. ......... 600/401 |
| 2001/0009973 A1 | 7/2001 | Miwa ........................ 600/399 |

FOREIGN PATENT DOCUMENTS

| | | |
|---|---|---|
| EP | 0 850 591 A1 | 7/1998 |
| JP | 6-142051 | 5/1994 |
| JP | 7-171113 | 7/1995 |
| JP | 8-126611 | 5/1996 |

OTHER PUBLICATIONS

Patent Abstracts of Japan, vol. 018, No. 451 (C-1241) Aug. 23, 1994 with respect to JP 6-142051 of May 24, 1994.

* cited by examiner

*Primary Examiner*—Max Hindenburg
*Assistant Examiner*—H. Q. Nguyen
(74) *Attorney, Agent, or Firm*—Fitzpatrick, Cella, Harper & Scinto

(57) ABSTRACT

A noncontact tonometer is disclosed that stores, into a storage unit, the image of an anterior ocular segment immediately before an intraocular pressure value is measured, and that, if an anomaly is found in the measurement result, facilitates the specification of the reason of the anomaly by automatically displaying the image of the anterior ocular segment that was acquired in advance.

10 Claims, 15 Drawing Sheets

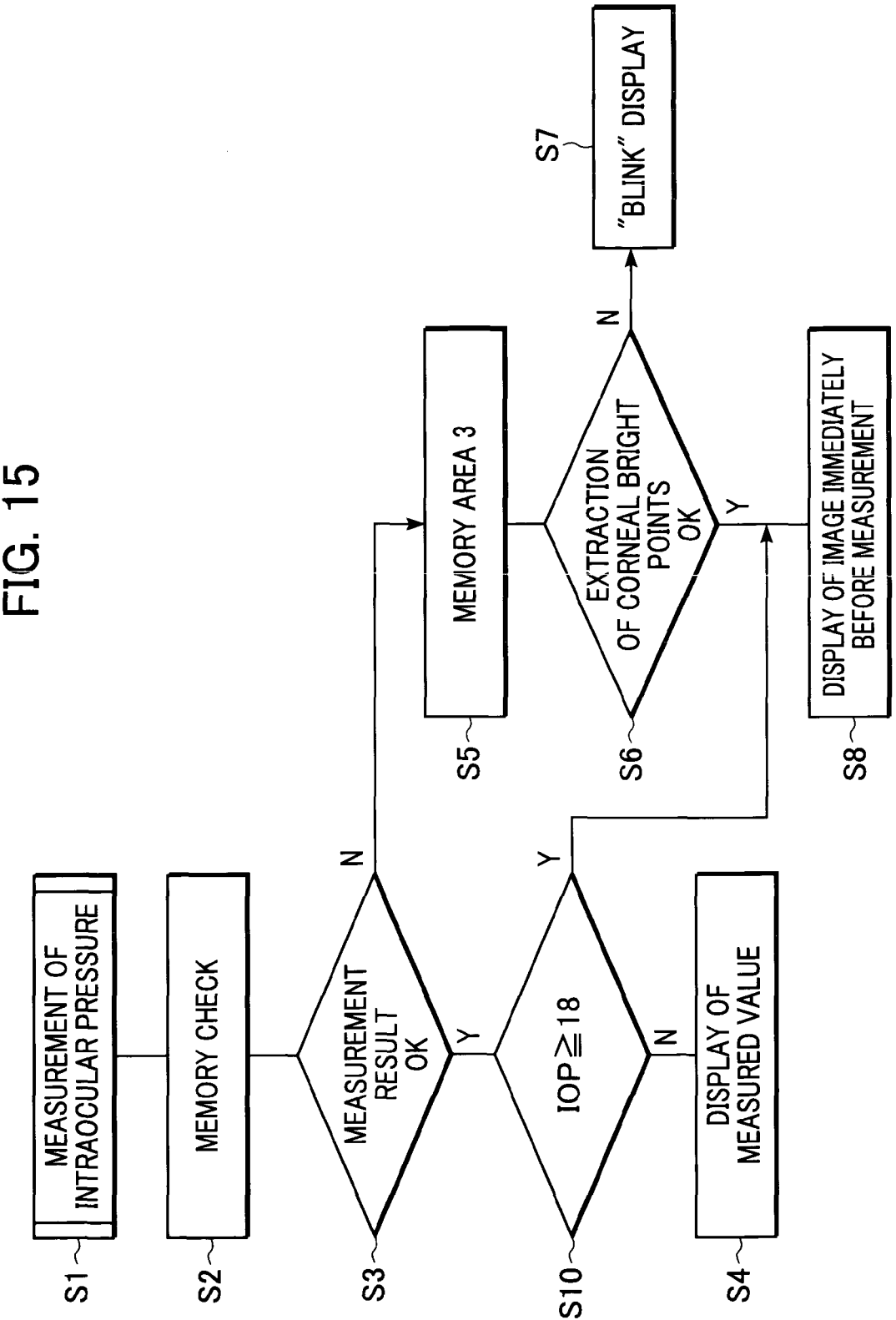

NONCONTACT TONOMETER

BACKGROUND OF THE INVENTION

1. Field of the Invention

The present invention relates to a noncontact tonometer that calculates the value of an intraocular pressure by an optical sensing means when air is blown onto an subject eye and the cornea thereof is deformed.

2. Description of the Related Art

The noncontact tonometer is represented by an air-puff tonometer developed by Bernard Grolman and set forth in U.S. Pat. No. 3,585,849. In this type of noncontact tonometer, a puff of air is blown onto the surface of a subject's eye from a nozzle at a distance of 11 mm from the cornea of the eye. After the applanation of the cornea is optically detected, a value is determined by means of the time that has elapsed prior to the applanation, and the value is calibrated by the Goldmann type intraocular tonometer, whereby an intraocular pressure value is calculated. An accurate intraocular value is obtained by using the Goldmann's principle.

During the past thirty years many improved tonometers have been proposed. In particular, the alignment between the subject eye and the air-blowing nozzle is a major contributing factor to measurement errors. In recent years, therefore, a tonometer is proposed that can perform automatic alignment with an alignment accuracy of $\frac{1}{10}$ mm, by projecting a light flux to the subject's eye and receiving the reflected light.

However, a subject's eye is not always at rest. If a fixation disparity of the subject eye occurs or the eye blinks immediately before air blowing, an accurate measured value cannot be obtained, which results in measurement error, thus requiring reexamination. The noncontact tonometer instantaneously performs a measurement, and therefore, when it makes a measurement error, it can not be determined whether its measurement failure is attributable to a movement of the subject's eye or a blink thereof.

As a conventional art, an ophthalmic instrument that, after having observed a subject's eye, photographs its anterior ocular segment, and stores the photographed image thereof, is disclosed in Japanese Patent Laid-Open No. 6142051. This invention is for storing the images of the anterior ocular segment under measurement, and displaying a predetermined time after the measurement, whereby it is checked by still images whether the measured result is affected by an eyelid and/or eyelashes.

Also, Japanese Patent No. 3108261 discloses a noncontact tonometer such that an examiner objectively determines the reliability of the measured result of an intraocular pressure by checking the images of the anterior ocular segment of a subject eye under applanation.

In the above-described Japanese Patent Laid-Open No. 6-142051, it is known from the descriptions of the embodiments thereof that still images are displayed after each measurement. In actuality, errors resulting from the hanging-down of eyelids and/or eyelashes occur about ten percent of the time, and proper measurement can occur approximately 90 percent of the time. Meanwhile, when numerous examinations need to be performed, the measurement of intraocular pressure must be performed with sufficient rapidity and accuracy.

In this case, if still images are displayed for several seconds with every measurement, an alignment operation of the other eye cannot be subsequently performed, thereby reducing efficiency. Furthermore, the examiners who check such still images must observe even the still images that involve no measurement problem. As a consequence, there is a risk that the examiners cannot afford to direct sufficient attention to the still images that involve measurement problems due to the interference of eyelids and/or eyelashes.

Meanwhile, the Japanese Patent No. 3108261 is for displaying photographed results of a cornea onto which air is blown and which has been subjected to applanation. Under the applanation condition, however, the reflected light flux of a projected light flux for alignment detection that has been projected onto the cornea is not imaged on an image pickup device, so that the misalignment between the subject eye and the apparatus is subtle and does not allow easy determination thereabout.

In some illustrated embodiments of the Japanese Patent No. 3108261, it is described that the timing of photographing is set immediately before and after the injection of air, and that the misalignment between a reflected image of a cornea and an index image is checked by a visual inspection using a photographed image immediately before the air injection. However, the subtle determination whether the amount of the misalignment is allowable is difficult to understand. Even if, after having measured an intraocular pressure, the examiner checks the displayed images immediately before and after the air injection, and finds that there is subtle misalignment therebetween, the examiner would be at a loss as to how to determine when the measured value becomes the same as that immediately before the air injection.

SUMMARY OF THE INVENTION

It is an object of the present invention to solve the above-described problems and provide a noncontact tonometer that can easily determine whether the measurement of intraocular pressure has been properly performed.

To achieve the above-described object, the present invention provides a noncontact tonometer in which the image of the anterior ocular segment is stored in the storage unit immediately before air is blown onto the cornea, and in which the stored image of the anterior ocular segment is displayed on a display unit based on the measured result.

Further objects, features, and advantages of the present invention will become apparent from the following description of the preferred embodiments with reference to the attached drawings.

BRIEF DESCRIPTION OF THE DRAWINGS

FIG. 15 is a flowchart of what occurs when the value of intraocular pressure has exceeded the standard value.

DESCRIPTION OF THE PREFERRED EMBODIMENTS

Figure 1:
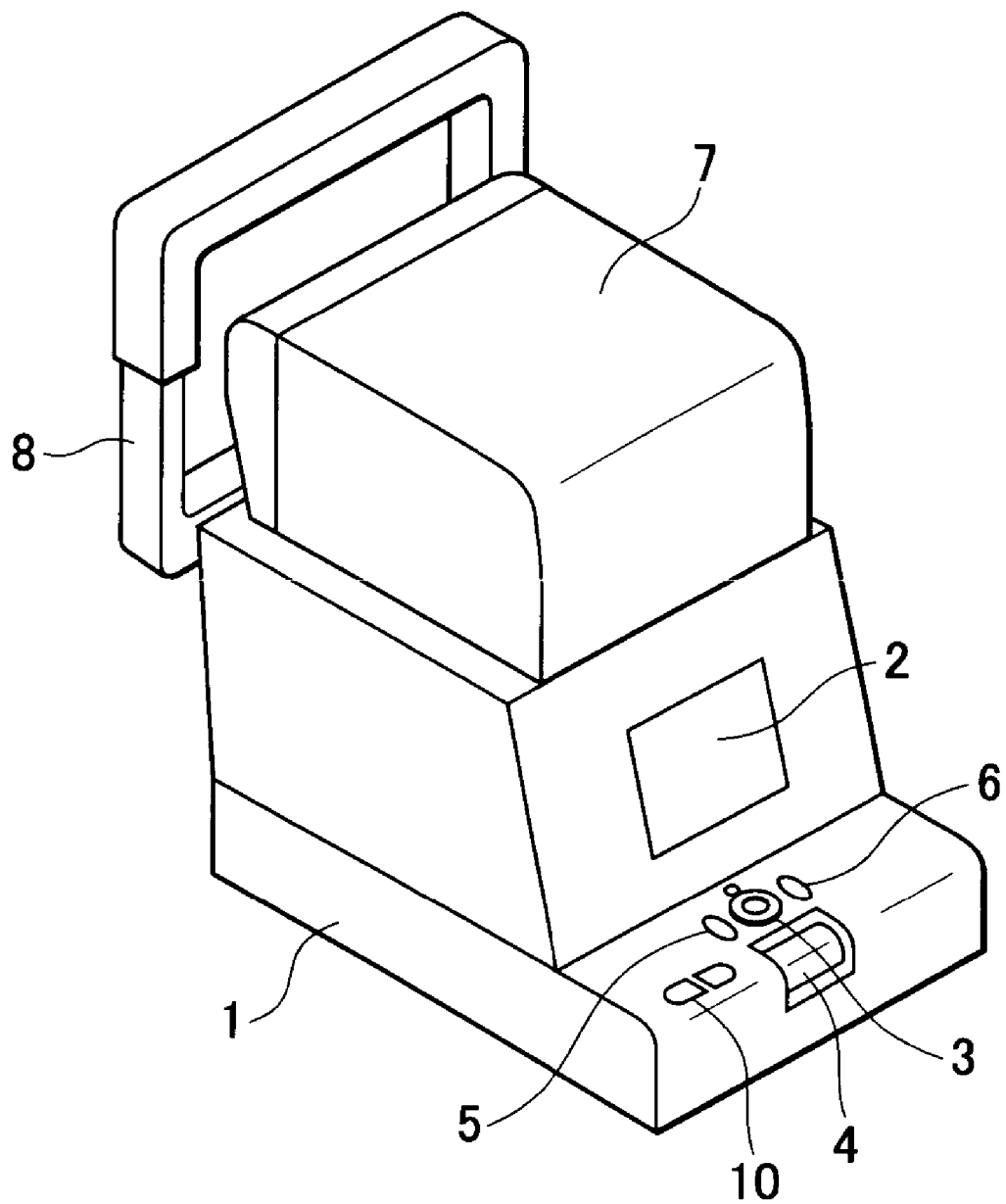
FIG. 1 is an external view of a noncontact tonometer according to an embodiment of the present invention, as viewed from the side of an examiner.
Figure 2:
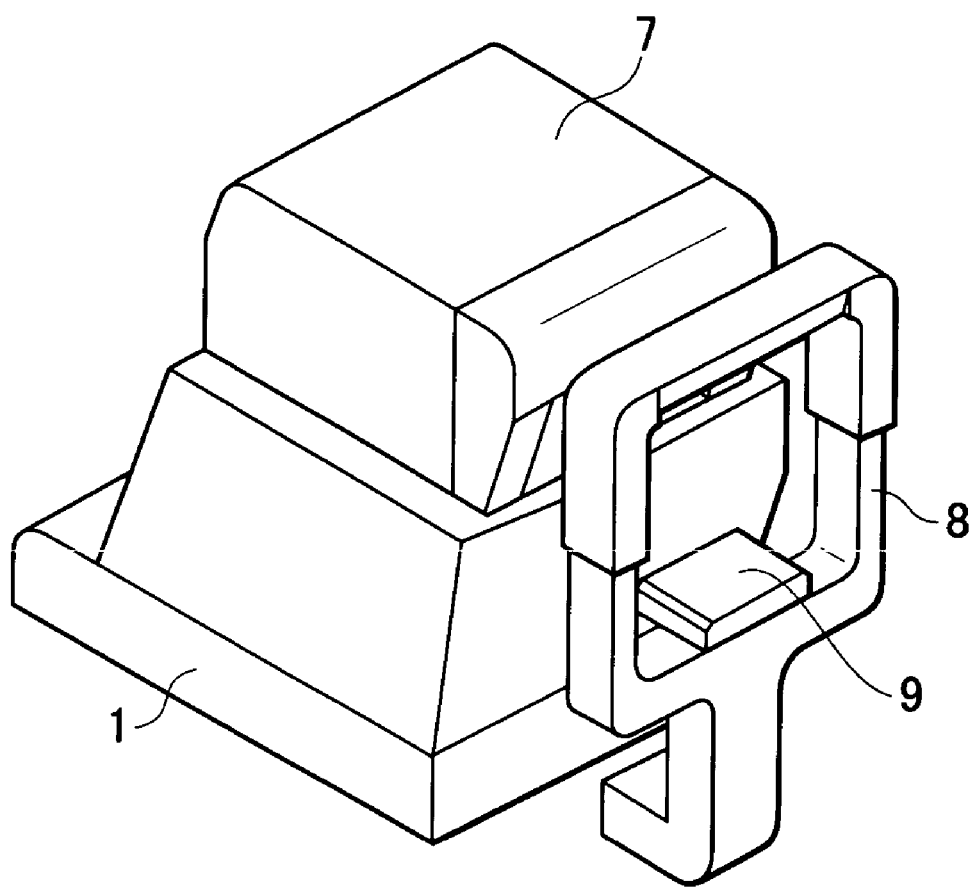
FIG. 2 is an external view of this noncontact tonometer, as viewed from the side of an subject eye.

Hereinafter, the present invention will be described in detail on the basis of the illustrated embodiment. FIG. 1 is an external view of a noncontact tonometer according to an embodiment of the present invention, as viewed from the side of an examiner, and FIG. 2 is an external view thereof as viewed from the side of an subject's eye. On the surface in the main body section 1, operated by the examiner, there is provided a monitor 2 comprising liquid crystals and a CRT (Cathode-Ray Tube) for displaying measured values and images of a subject's eye or the like and selecting the setup of various equipment, a trackball 3 for operating the display screen of the monitor 2 and roughly aligning a measurement section with a subject eye, a roller 4, a printer print switch 5, and a measurement start switch 6.

The measurement section 7 is placed on the main body section 1, and is arranged to be movable in the up-and-down, right-and-left, and back-and-forth directions relative to the main body section 1, in order to perform alignment with a subject eye to measure the intraocular pressure value. The measurement section 7 is adapted to be movable relative to the main body section 1 within the range of 90 mm along the right-and-left direction, the range of 40 mm along the back-and-forth direction of the subject eye E, and the range of 30 mm along the up-and-down direction. As means for moving the measurement section 7, one that performs driving by electrical control as set forth in Japanese Patent Laid-Open No. 8-126611 may be used, or alternatively, a type that has a measurement section mounted on a movable stand and that likewise moves the movable stand by operating a joystick, may be employed.

On the opposite side of the surface in the main body section 1, operated by the examiner, there is provided a head receiving member 8. The head receiving member 8 has a chin rest 9 provided for resting the chin of an examinee, and is arranged to be able to move the chin rest 9 in the up-and-down direction by a chin rest up-and-down switch 10.

Figure 3:
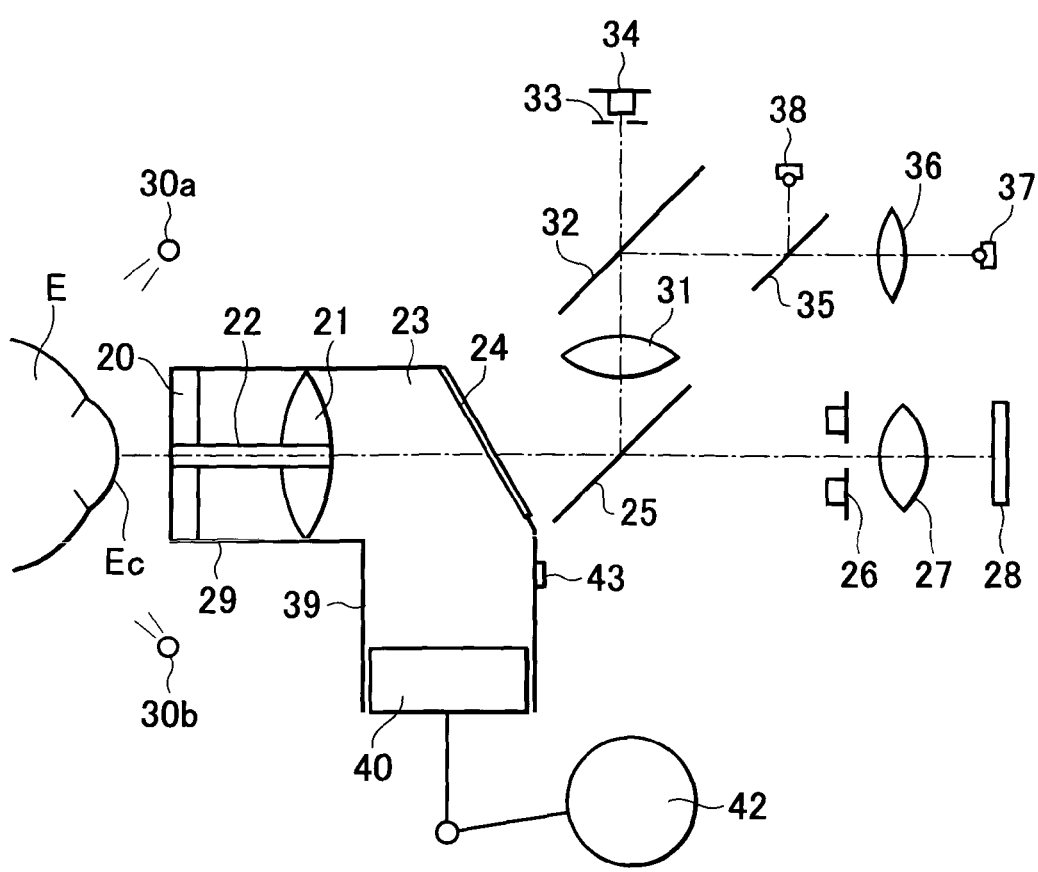
FIG. 3 is a constructional view of an optical system according to the present invention.

FIG. 3 is a constructional view of an optical system of the measurement section 7. A nozzle 22 is disposed on the central axis of a parallel plane glass 20 and an objective lens 21 so as to be opposed to the cornea Ec of the subject eye E. Behind them, an air chamber 23, an observation window 24, a dichroic mirror 25, a prism diaphragm 26, an image forming lens 27, and an image pickup device 28 are arranged in sequence. These constitute a light-receiving optical path for an observation optical system with respect to the subject eye E, and an optical path for alignment detection.

The parallel plane glass 20 and the objective lens 21 are supported by an objective lens barrel 29. External-eye illumination sources 30a and 30b for illuminating the subject's eye E are provided outside of the objective lens barrel 29.

In the reflection direction of the dichroic mirror 25, there are provided a relay lens 31, a half mirror 32, an aperture 33, and a light receiving device 34. Here, the aperture 33 is disposed in a position conjugate to the reflected image of a cornea irradiated by a measurement light source described later when the cornea Ec has been subjected to a predetermined amount of deformation, and the aperture 33 is treated, together with the light receiving device 34, as constituting a deformation detection light-receiving optical system when the cornea Ec is deformed along the visual axis direction.

In the incident direction of the half mirror 32, there are provided a half mirror 35, a projection lens 36, and a measurement light source 37 comprising a near-infrared LED (Light-Emitting Diode) used for measurement and also for alignment with the subject's eye E. On the other hand, in the incident direction of the half mirror 35, there is provided a light source 38 for fixation, comprising an LED to which an examinee fixes the vision line thereof.

In the air chamber 23, a piston 40 is fitted into a cylinder 39 constituting a portion of the air chamber 23, and the piston 40 is driven by a solenoid 42. Here, a pressure sensor 43 for monitoring the internal pressure of the air chamber 23 is provided therein.

Figure 4:
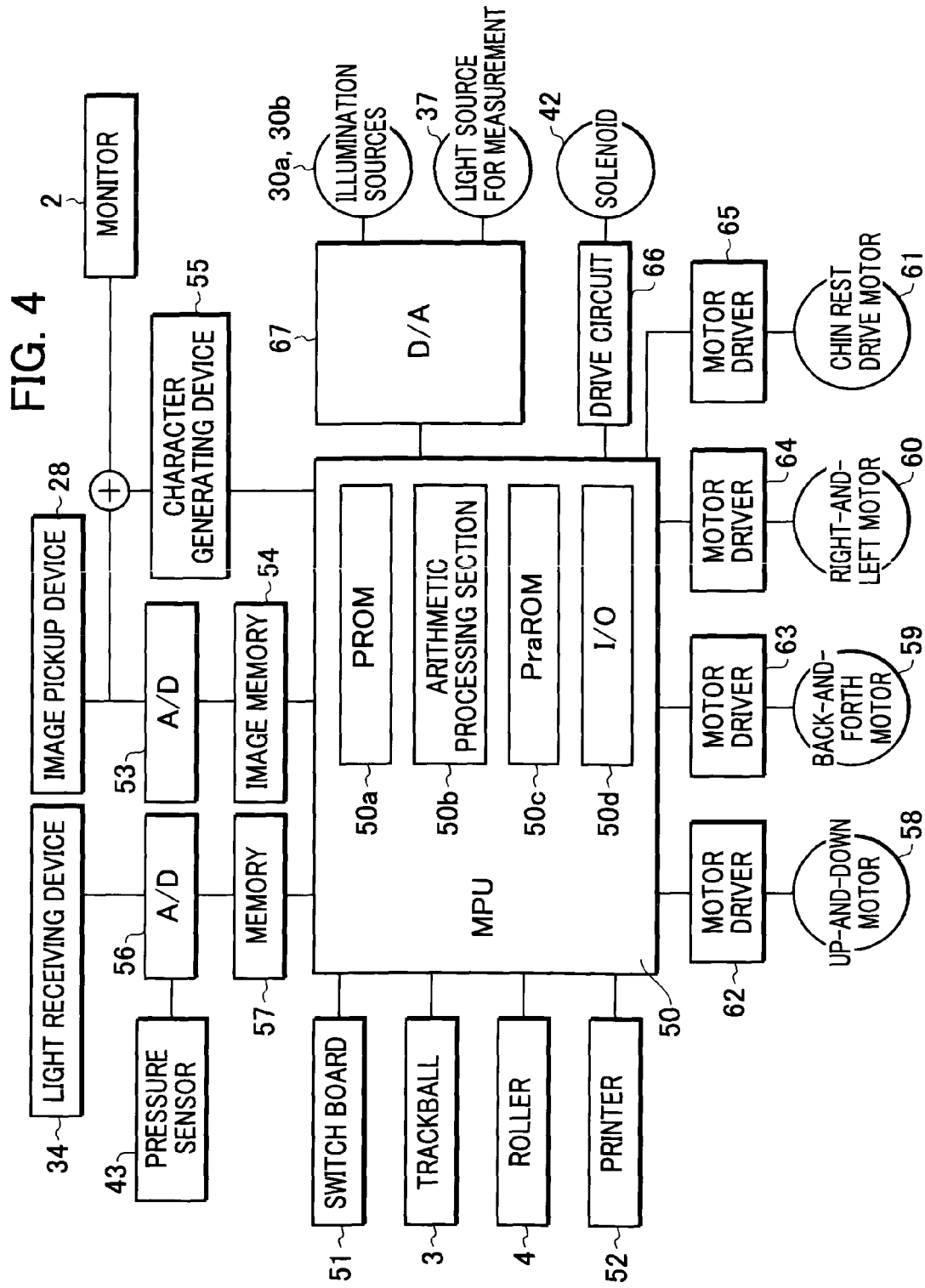
FIG. 4 is an electrical block circuit diagram of the entire system of the present invention.

FIG. 4 is an electrical block circuit diagram of the entire system when the alignment of the measurement section 7 is performed by electrical control. An MPU (Microprocessor Unit) 50 for controlling the entire system includes a PROM (Programmable Read Only Memory) 50a for storing programs, an arithmetic processing section 50b for performing arithmetic computation on data acquired from various devices such as the light receiving device 34 and the image pickup device 28, a parameter PROM 50c for storing data for correcting intraocular pressure values, an I/O 50d for controlling input/output of data, and so on.

Connected to the ports of the MPU 50, are a switch board 51 having a measurement start switch 6, a printer print switch 5 and the like provided thereon, a trackball 3 for roughly aligning the measurement section 7 with the subject eye E, a rotary encoder incorporated in the roller 4, and a printer for printing the measured results.

Image signals of the anterior ocular segment images of the subject eye E photographed by the image pickup device 28 are stored into an image memory 54 by an A/D converter 53 via digital data, and are again connected to the MPU 50. The MPU 50 extracts the reflected images of the cornea of the subject eye E and performs alignment detection based on the images stored in the image memory 54. The image signals of the anterior ocular segment images photographed by the image pickup device 28 are combined with signals from a character generating device 55, and the anterior ocular segment images and the measured values and the like are displayed on the monitor 2.

A light receiving signal obtained by the image pickup device 28 and a pressure signal detected by the pressure sensor 43 in the air chamber 23 are amplified, and after having been converted into digital data by an A/D converter 56, they are stored into a memory 57 in sequence. When the MPU 50 detects the peak value of the A/D converted light receiving signal from the light receiving device 34, it reads the A/D converted data of the light receiving device 34, and stores them into the memory 57. All of the light receiving signals and the pressure signals are stored into the memory 57.

An up-and-down movement motor 58, a back-and-forth movement motor 59, a right-and-left movement motor 60, and a chin rest drive motor 61 are driven by commands from the MPU 50 through motor drivers 62, 63, 64, and 65, respectively. The solenoid 42 is drive-controlled by a command from the MPU 50 through a drive circuit 66. The outputs of the measurement light source 37 and the external eye illumination sources 30a and 30b are connected to a D/A converter 67, and the light amount thereof can be varied by a command from the MPU 50.

During the measuring operation, the light source 38 for fixation is turned on, and the measurement start switch 6 is pushed in a state where the subject eye E is caused to fix the vision line to the light source 38. The reflected images of the cornea irradiated by the illumination light from the external eye illumination sources 30a and 30b pass through the parallel plane glass 20, the objective lens 21, the air chamber 23, the observation window 24, the dichroic mirror 25, the prism diaphragm 26, and the image forming lens 27, and arrive at the image pickup device 28. When the reflected images of the cornea have been extracted by the image pickup device 28, the amount of deviation from the proper position is calculated, and the objective lens barrel 29 is properly aligned with the cornea Ec by auto-alignment control by which a correction for compensating for the misalignment portion is performed.

Simultaneously, the MPU 50 drives the solenoid 42, and the air within the air chamber 23 is compressed by the piston 40 pushed up by the solenoid 42, thereby jetting from the nozzle 22 toward the cornea Ec of the subject's eye E, as an air pulse.

The light flux from the measurement light source 37 is converted into parallel light by the projection lens 36, then it is bent by the half mirror 32, and after having been once imaged in the nozzle 22 by the relay lens 31, it irradiates the cornea Ec of the subject's eye E. The reflected light flux of the cornea Ec irradiated by the measurement light source 37 passes through the parallel plane glass 20 and the objective lens 21 outside the nozzle 22. Then the reflected light flux is reflected by the half mirror 25, and after having transmitted through the half mirror 32, it is optoelectronically converted by the light receiving device 34 into an electrical signal. In this case, the relay lens 31 is designed to form a cornea reflected image having a size substantially equal to that of the aperture 33 when the cornea Ec is subjected to the predetermined amount of deformation.

Figure 5:
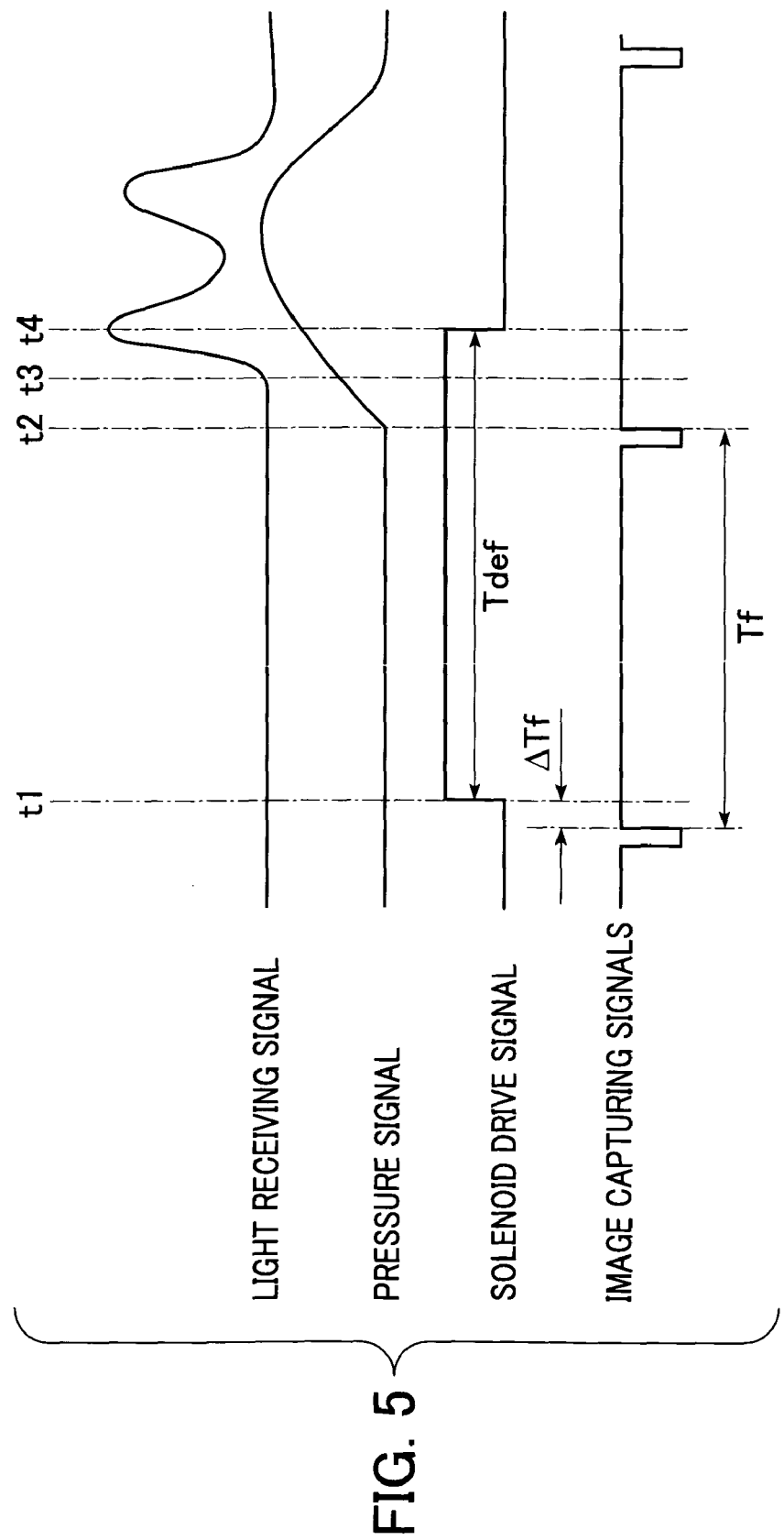
FIG. 5 is a time chart showing capture timings for various signals.

FIG. 5 is a time chart showing a light receiving signal from the light receiving device 34, a detection signal from the pressure sensor 43, a drive signal of the solenoid 42, and recording timing signals from the image memory 54 until the completion of a measurement from the time when it is determined, based on the detection result by the image pickup device 28, that alignment has been achieved.

The time point t1 shown in FIG. 5 is a timing when it is determined that the alignment has been achieved, and when the solenoid 42 starts driving the piston 40. Therefore, at the time t1, the solenoid 42 begins to drive the piston 40, and the piston 40 begins to lift the cylinder 39. When the piston 40 moves by a predetermined amount, the pressure in the air chamber 23 begins to rise, and the pressure-rise starting time is the time point t2. When the pressure in the air chamber 23 begins to rise, air jets from the nozzle, and the cornea Ec begins to deform at the time point t3. When the cornea Ec deforms by the predetermined amount, the amount of received light of the light receiving device 34 exhibits the maximum value at the time point t4.

When an air blowing force decreases after the deformation goes on, the deformation of the cornea Ec begins to restore. At the time of the predetermined amount of deformation, the amount of received light of the light receiving device 34 again increases, and finally diminishes. The pressure signal of the pressure sensor 43 has a mountain-shaped pattern with the peak value thereof appeared after the predetermined amount of deformation of the cornea Ec. The drive signal of the solenoid 42 reduces excess air blowing after having detected deformation, by stopping a drive current at the time of the predetermined amount of deformation of the cornea Ec, that is, at the time point t4.

The drive duration Tdef of the solenoid 42 is approximately 20 ms. The image capturing signals capture images for each field with Tf=16.7 ms (Tf: field time). In order to set the time Tf so that it occurs as immediately before deformation detection as possible, the drive signal of the solenoid is arranged to be A/D converted with a little delay time ΔTf provided so that the capturing stop time becomes the time point t2.

In this manner, the images of the anterior ocular segment that have been captured under timing control are stored into the image memory 54. The light receiving signal and the pressure signal are A/D converted by the A/D converter 56 from the time point t2, and the converted data are stored into the memory 57 by the two field lengths of data.

Figure 6:
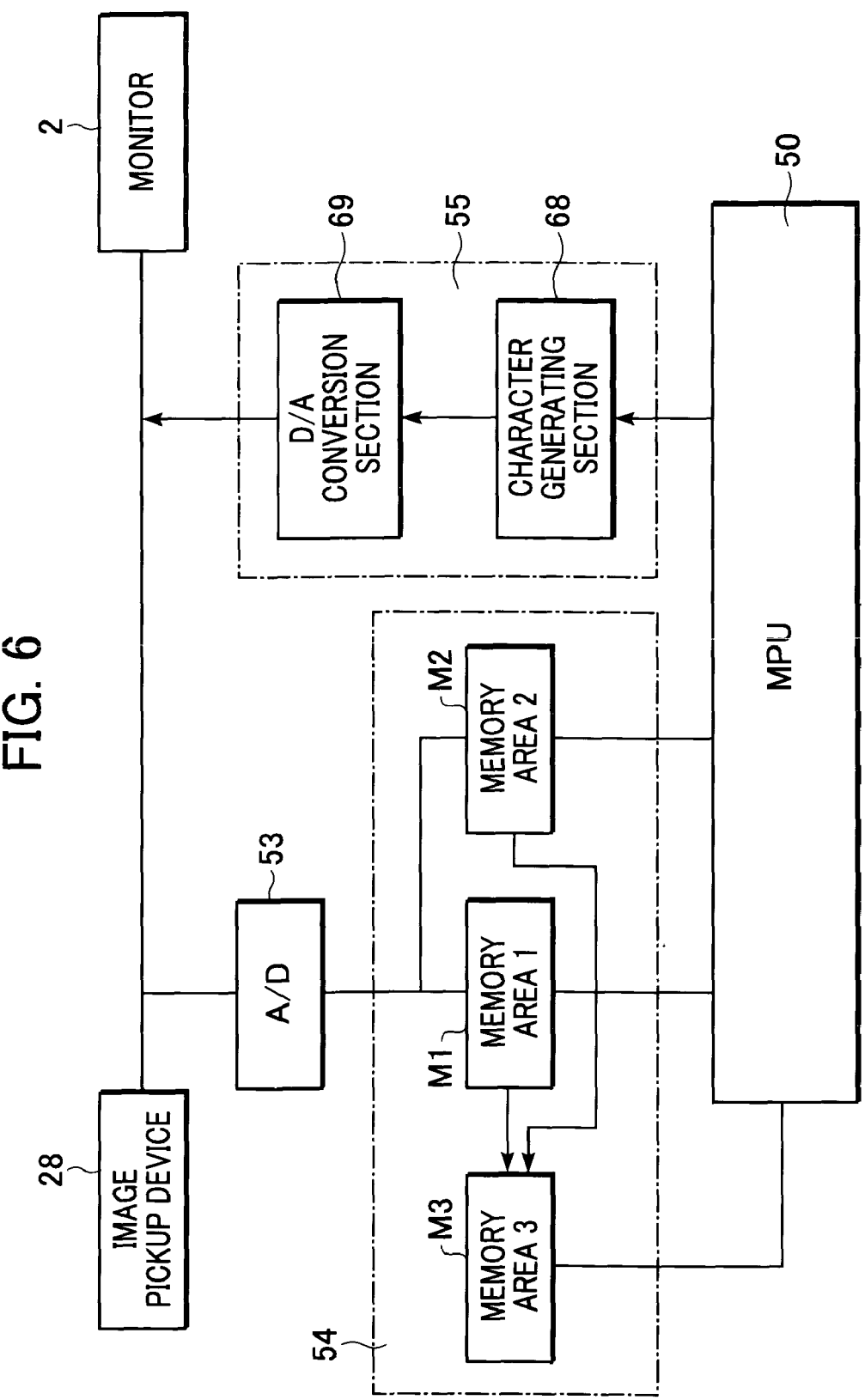
FIG. 6 is a block diagram showing the flow of processing of image data.

FIG. 6 is a block diagram showing the flow of processing of image data captured by the image pickup device 28. During auto-alignment, images A/D converted for each field are repeatedly overwritten and stored into a memory area 1 (M1), a memory area 2 (M2), the memory area 1 (M1), and the memory area 2 (M2) in the image memory 54, in this order. The time interval between capturing operations is one field time of approximately 17 ms. Images stored in each of the memory areas is subjected, by MPU 50, to processing of pupil extraction and position detection when the pupil is detected, and to processing of bright point extraction and position detection when corneal reflex bright points are detected. Because the time required for this processing is arranged to be less than about 17 ms, the images of the anterior ocular segment can be continuously processed at the field rate.

When video signals from the time point t1 to the time point t2 shown in FIG. 5 are captured, the images are transferred to the memory 3 (M3). After the measuring operation, the measurement result is calculated based on the light receiving signal and the pressure signal captured into the memory 57. If the measurement has been properly performed, the image data in the memory 3 (M3) is maintained, and is arranged to be overwritable at the next measurement. On the other hand, if the measurement has not been properly performed, it is checked whether corneal reflex bright points have been able to be extracted from the image in the memory 3 (M3).

If bright points could be extracted at an immediately preceding field but can not be extracted at the current field, it is determined to be a blink error because of cornea reflected light shaded by the eyelid. On the other hand, if corneal reflex bright points are extracted, the image data thereof has a target mark indicating a proper position generated by the character generating section 68 of the character generating device 55, and in combination with image data in the memory area 3 (M3), this image is converted into an analog video signal by the D/A conversion section 69, and the monitor 2 displays the image.

Figure 7:
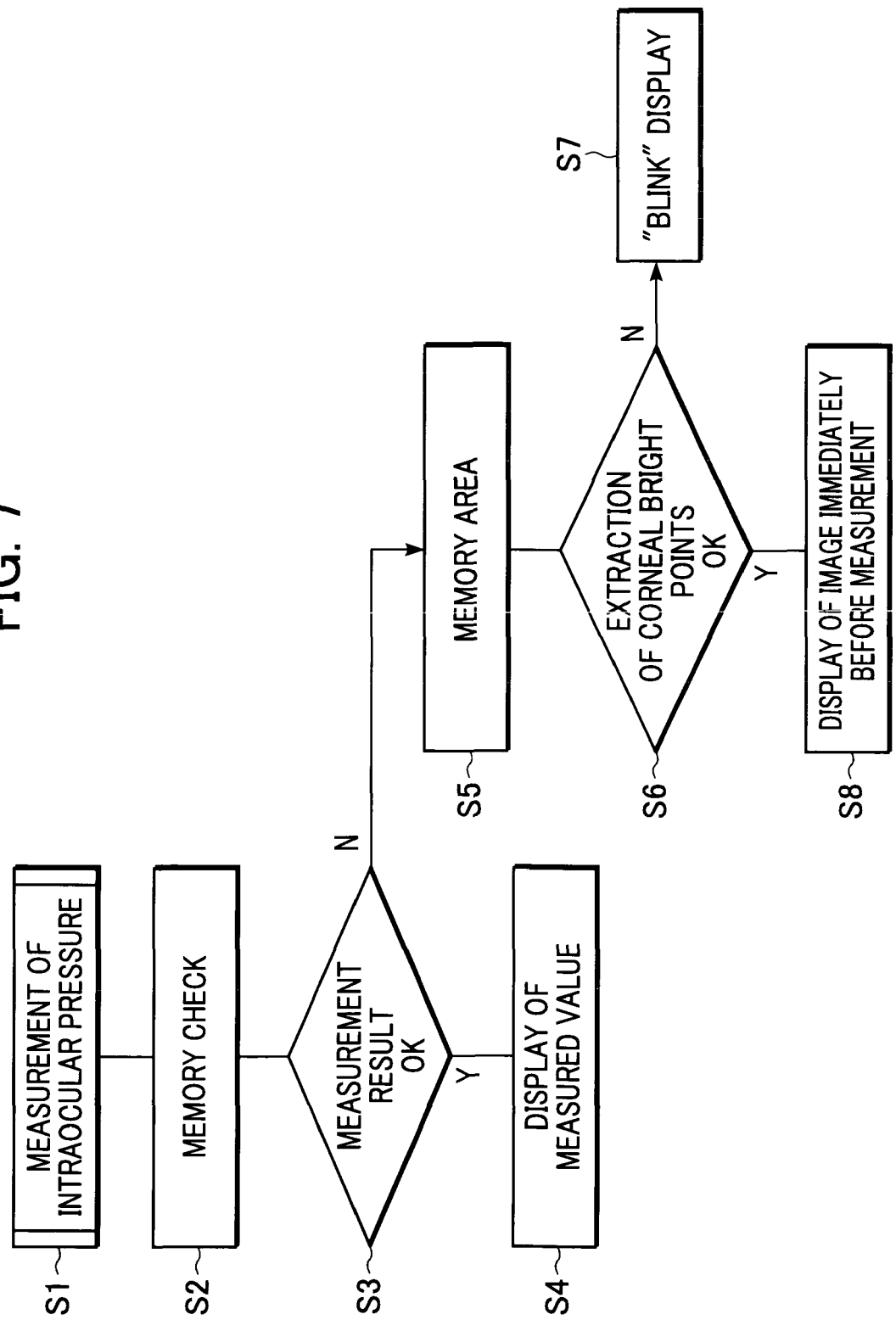
FIG. 7 is a determination flowchart for image display.

In this way, the determination regarding the image display of the measurement result is performed according to a flowchart in FIG. 7. In step S1, which is a series of intraocular pressure measurement operations, the auto-alignment is completed, and after the solenoid 42 is driven, air is blown from the nozzle 22 onto the cornea Ec. After step S1 has been accomplished, the pressure signal and the light receiving signal are captured into the memory 57 in step S2. In the next determination step S3, it is determined whether a measured value has been obtained under a predetermined determination condition. If it is determined that a measured result has been obtained, the processing transfers to step S4, where the measured value is converted into an intraocular pressure value, and the intraocular pressure value is displayed on the monitor 2.

In determination step S3, if it is determined that a measured value has not been obtained, the processing transfers to step S5, where an image is transferred from the memory area 1 or 2 to the memory area 3. In determination step S6, it is determined whether the corneal bright points have been extracted from the memory area 3. If the corneal bright points cannot be extracted, it is checked whether the corneal bright points are extracted from the immediately preceding image, that is, from the image that has been determined to be in proper alignment and that is stored in the memory area 2 or 1, and it is therefore determined that there has been a blink. Thus the processing transfers to step S7.

Figure 8:
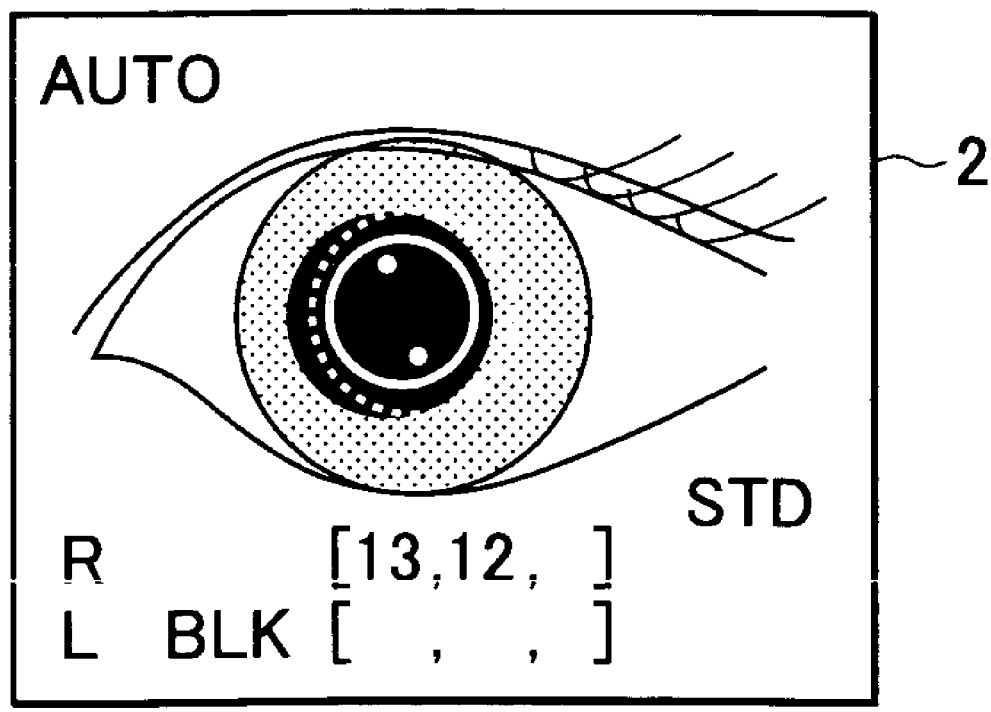
FIG. 8 is a view showing a screen displaying a blink error.

In step S7, the character generating section 68 generates characters "BLK" and forms columns for measured values. As shown in FIG. 8, a blink error is displayed on the monitor 2, in combination with real time video signals. If it is determined, in determination step S6, that the corneal bright points have been extracted, the monitor 2 is caused to display the images in the memory area 3 in step S8, as described later.

Figure 9A:
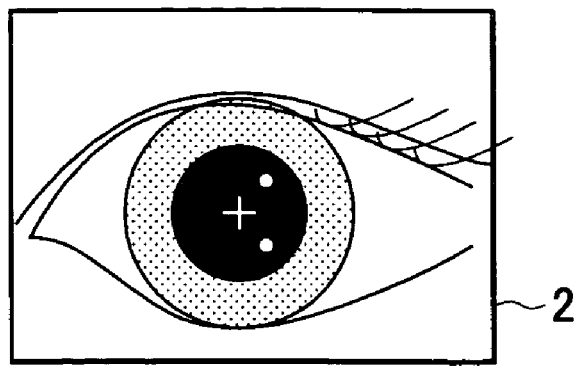
FIGS. 9A to 9D are views illustrating still image displays.
Figure 9B:
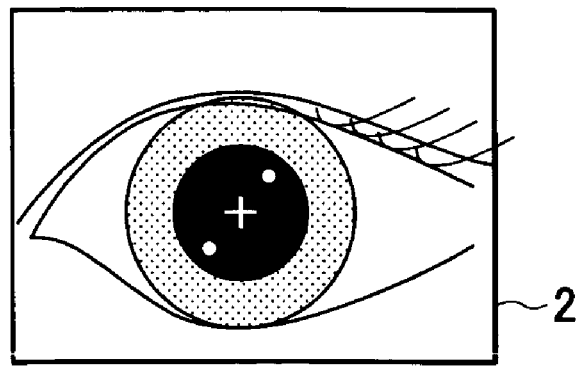
Figure 9C:
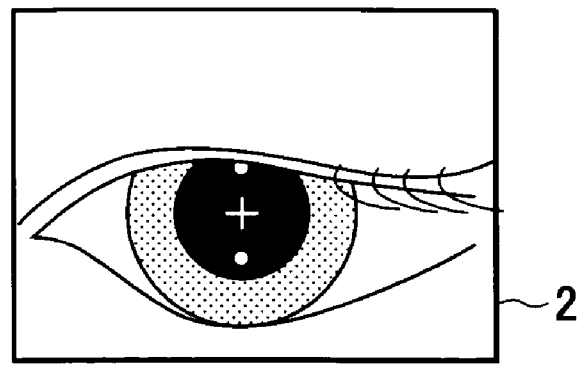
Figure 9D:
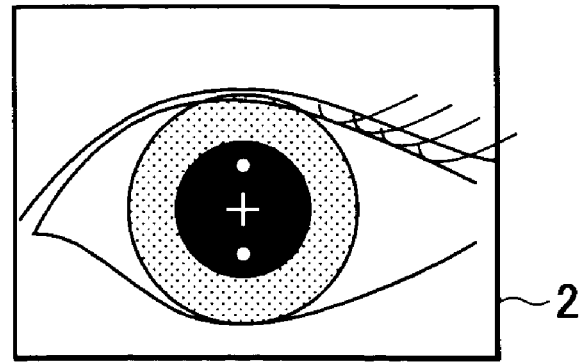

FIGS. 9A to 9D show images of an eye. Each image is combined with a target mark indicating a proper alignment position by the character generating section 68 of the character generating device 55. Cross hairs shown at the center of a pupil are a target mark indicating an alignment position. By checking FIG. 9A, an examiner can determine that a measurement error has occurred because a subject's eye E has moved at the moment of measurement and is measured so as to be slightly deviated to the right. By observing FIG. 9B, it can be determined that the subject eye E has moved in the back/forth direction. Also, from FIG. 9C, it is determined that a measurement error has occurred because an eyelid hangs down. FIG. 9D shows that the subject eye E is in a correct measurement position.

Figure 10:
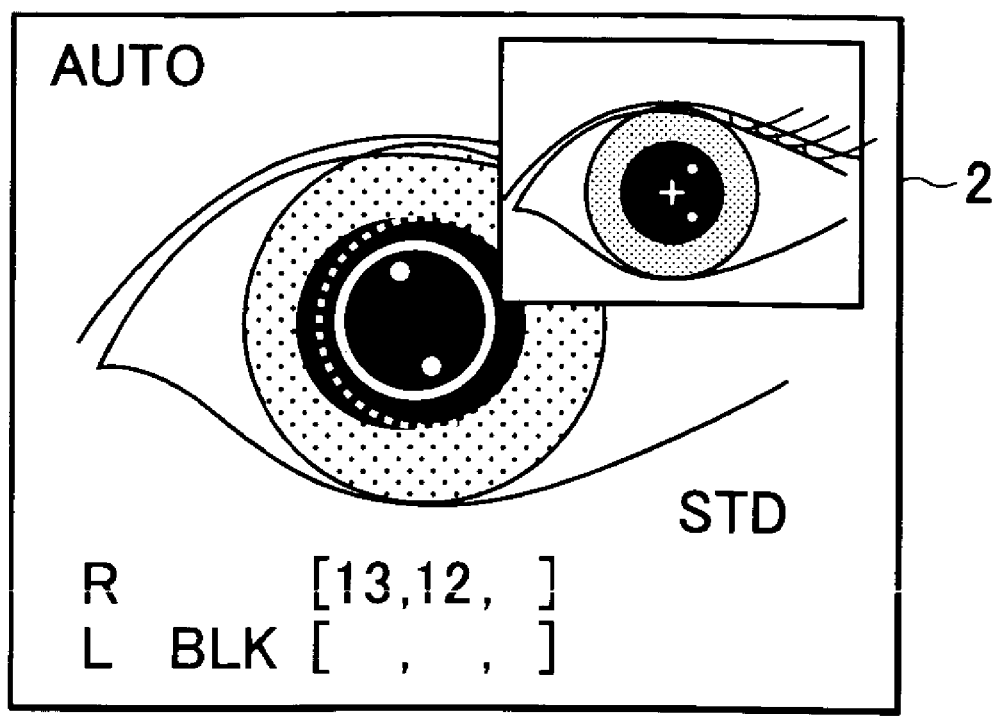
FIG. 10 is a view illustrating a combined image display.

FIG. 10 is a view illustrating a display on the monitor 2 including a plurality of images. In this way, image data in the memory area 3 is not displayed on the entire display screen, but on a portion thereof. This is because, with a tonometer, the operational distance between the nozzle 22 and the apex of the cornea EC is as short as 11 mm, and therefore, if the image is displayed on the entire screen with the real time picture hidden, there is a risk that the examiner might overlook that the present apparatus contacts the subject eye E. That is, this display method is one in which consideration is given to safety.

In the above-described embodiment, the image memory 54 has been divided into three memory areas, but the present invention is achievable with two memory areas, as well. Specifically, in measuring an intraocular pressure, image data immediately before the intraocular pressure measurement is the last data in one time measurement, and therefore, the image data immediately before intraocular pressure measurement is stored, for example, into the memory area 2. Here, the field immediately preceding the above-described image data is data subsequent to image data that has been determined to have accomplished alignment. It is determined, during this field time, whether this field has completed alignment, and hence, this image data is stored into the memory area 1. Thus, the present invention becomes attainable with the two memory areas.

After the measurement result has been obtained, the stored image data may be erased by a right/left switching operation for proceeding to the next measurement, or at the ON timing of the print switch or the ON timing of the start switch. Alternatively, the above-described stored image data may be overwritten at the next alignment after the measurement result has been obtained.

Figure 11:
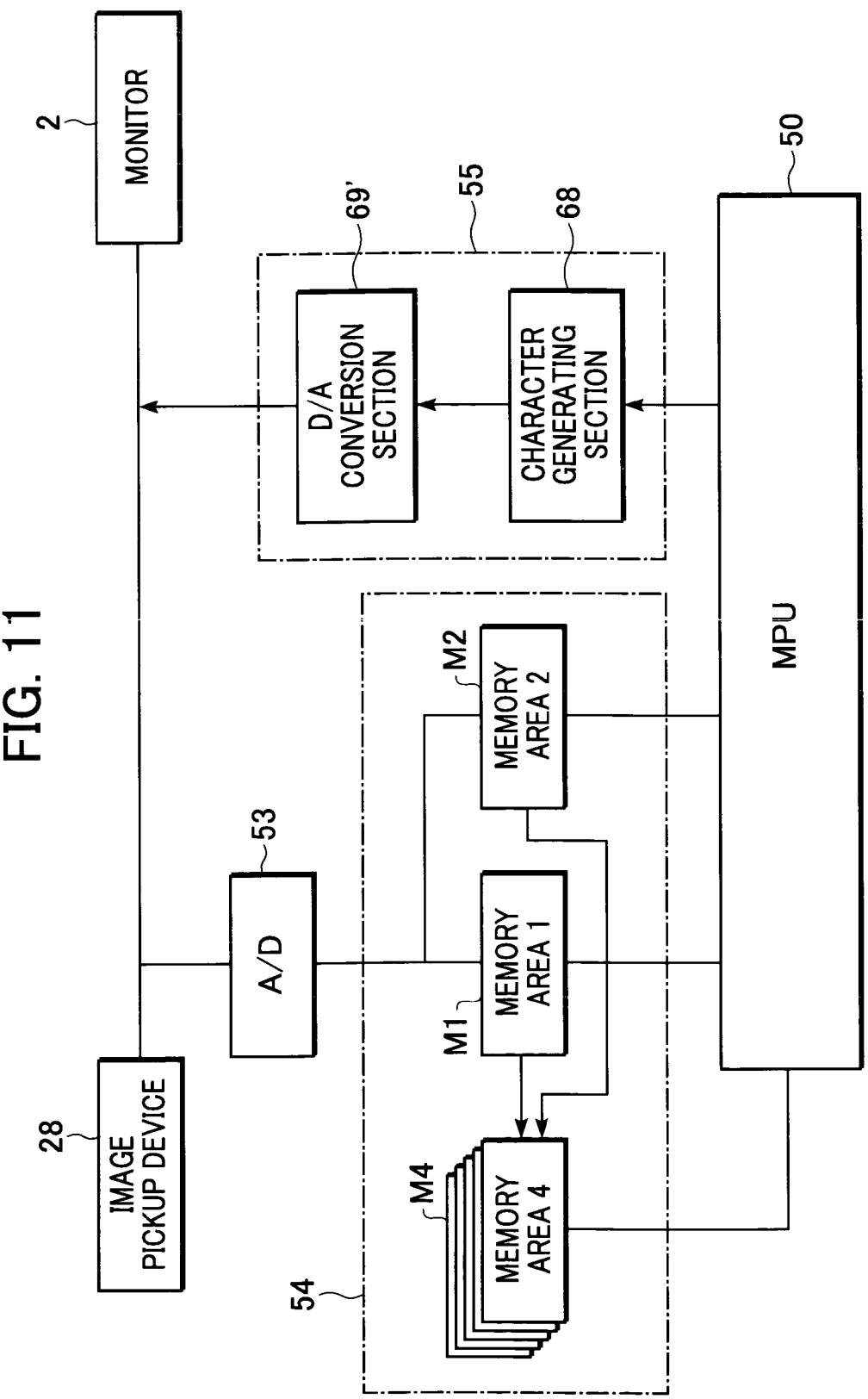
FIG. 11 is a block diagram showing the flow of processing of moving image data.

FIG. 11 is a modified view of FIG. 6. With moving images storage, there is provided a memory area 4 that can store more field images than the memory area 3. The field subsequent to the field that has been determined to have alignment completed, and the field immediately before a measurement are sequentially transferred to the memory area 4. Four or five fields out of the fields immediately before the measurement, and six or seven fields in total, of image data with a length of approximately 0.1 seconds, are stored into the memory area 4.

As illustrated in flowchart shown in FIG. 7, when the display of the measurement result is determined and the image immediately before measurement is displayed, the image data of each field in the memory area 4 is controlled by a D/A conversion section 69 so as to be displayed in combination with a real time picture, with each field having a field rate of forty.

That is, the field subsequent to the field that has been determined to have alignment completed is displayed for forty real-time fields; then the next field, which is the field immediately before measurement, is displayed for forty real-time fields; and the next field, which is the measurement field, is displayed for forty real-time fields, thus sequentially combining these fields. Therefore, slow reproduction still images of 240 to 280 fields in total with a length of 4 to 4.7 seconds, are displayed on a smaller screen portion at the upper right corner of the monitor 2, as shown in FIG. 12.

In this case, a switch (which is not shown in FIG. 1) that is exclusively for slow reproduction is disposed adjacent to the chin rest up-and-down switch 10, and thereby checks can be repeatedly made until the next measurement. When the slow reproduction is to be interrupted, touching any switch other than the switch that is exclusively for slow reproduction allows interruption.

Figure 12:
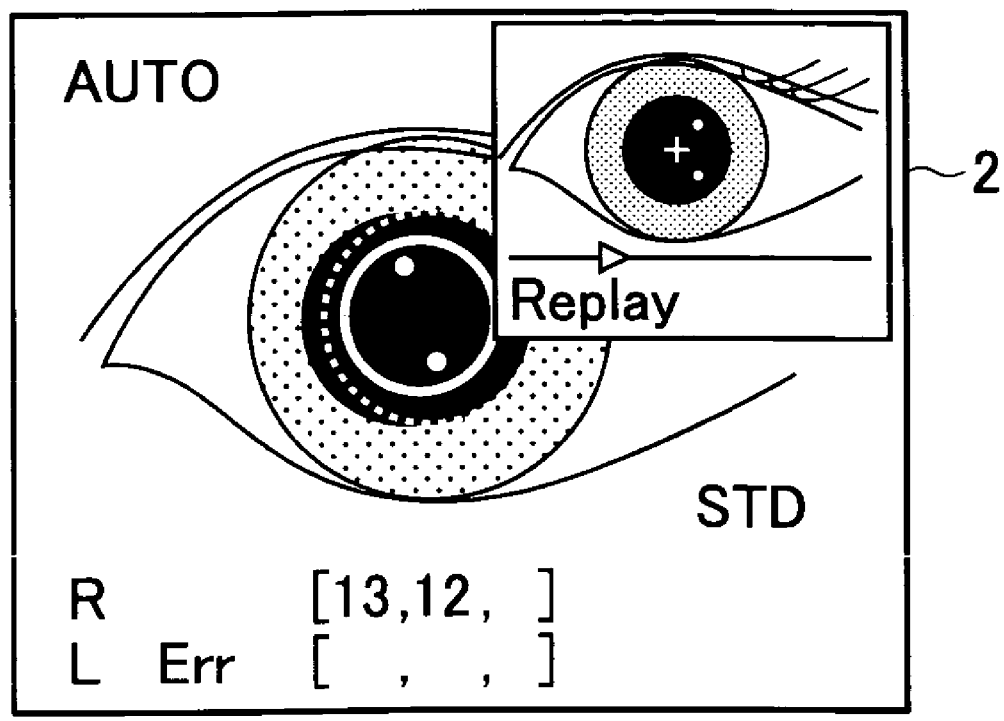
FIG. 12 is a view illustrating a moving image display.
Figure 13A:
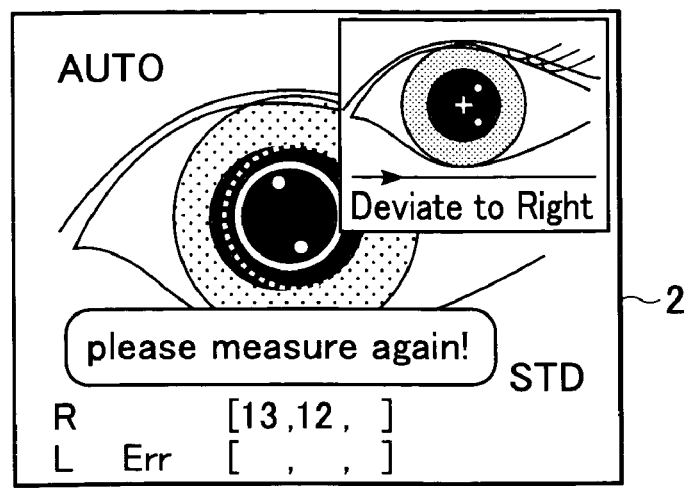
FIGS. 13A to 13C are views illustrating displays when measurement errors have occurred.
Figure 13B:
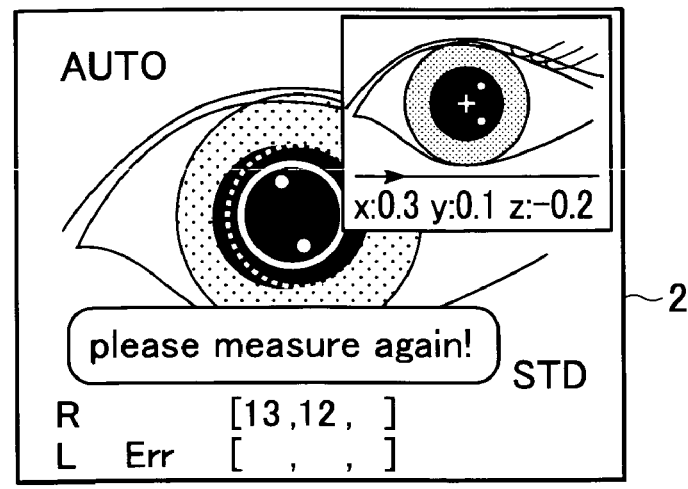
Figure 13C:
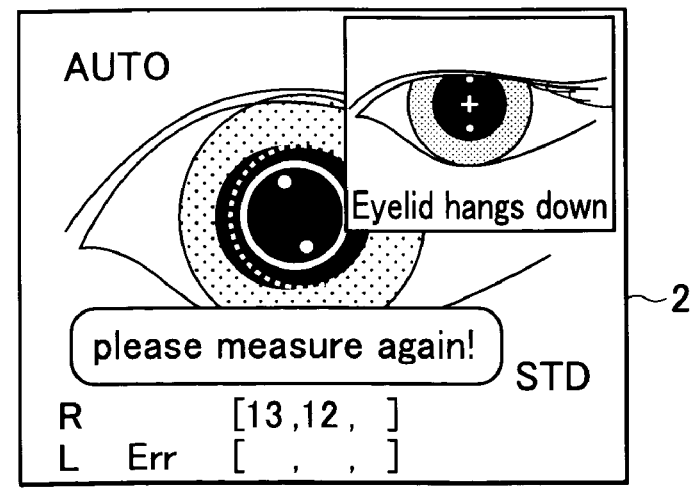

FIG. 12 is a view illustrating the normal display state of the monitor 2, and FIGS. 13A to 13C are views illustrating display states of the monitor 2 when measurement errors have occurred. Each of the smaller screens shows a still image, and each of the images behind the central messages is a real time image. FIG. 13A is for letting the examiner know that the subject's eye has moved. FIG. 13B shows a display on the smaller screen which indicates the amount of deviation due to the movement. FIG. 13C shows a display example in which the eyelid hangs down and has caused an error.

The time required to return to a normal screen from the representation of a displayed still image is set to a predetermined time of 5 to 6 seconds. When attempting to earlier clear the display of the still image, the display can be cleared by the trackball 3 and the roller 4, each of which is operated by the examiner, and a switch such as the printer print switch 5 and the measurement start switch 6.

Even when a measured value without measurement error is obtained, there are cases where it is desirable to display a still image. There are variations among eyelashes of individual examinees. In measuring the intraocular pressure, in some cases, measured values are not subject to adverse effects even if eyelashes hang down on the subject eye E. In other cases, however, eyelashes hanging down on the subject eye E causes the measured value to become higher by 5 to 8 mm Hg or more. In the intraocular pressure measurement by a noncontact tonometer, when the measured value exhibits 18 mm Hg or more, the examinee is usually to be subjected to a precise intraocular pressure measurement and/or fundus examination for screening.

However, it puts a large load on the examinee and the medical institutions that treat glaucoma patients having a high intraocular pressure, under the influence of eyelashes. Therefore, when a high intraocular pressure value is measured, it is first recommended to display the image immediately before the measurement and check whether eyelashes hang down on the subject's eye.

Figure 14:
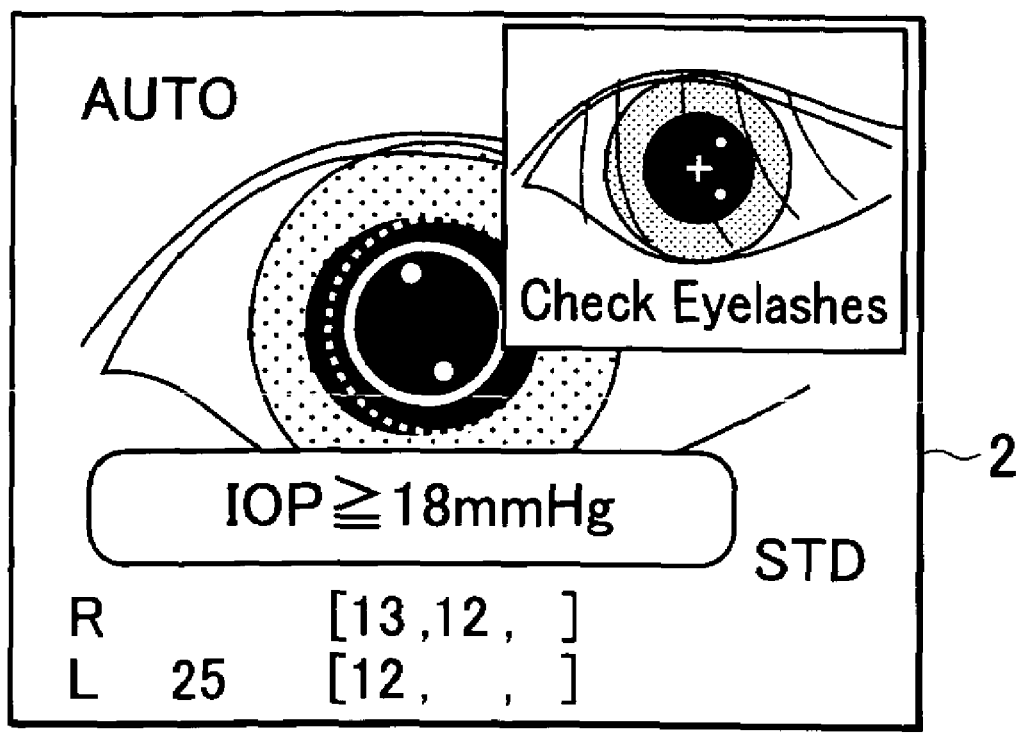
FIG. 14 is a view illustrating a still image when the value of the intraocular pressure has exceeded a standard value.

The capturing of images is performed in the same manner as that shown in FIG. 6 (block diagram). The intraocular pressure value is calculated from the pressure signal and the light receiving signal stored in the memory 57. If the measured intraocular pressure value IOP is 18 mmHg or more, it is displayed on the screen, as shown in FIG. 14. FIG. 15 is a flowchart of display control, and is a modified view of the flowchart shown in FIG. 7. In FIG. 15, when a measured value is obtained in determination step S3, it is determined, in step S10, whether the measured value is not less than a preset standard value 18 mmHg. If the measured value is not less than 18 mmHg, the processing transfers to step S8, and the display as shown in FIG. 14 is performed.

On the other hand, if the measured value is less than 18 mmHg, the processing transfers to step S4, and the monitor 2 displays the intraocular pressure value as usual. The above-described standard value 18 mmHg can be changed into 17 mmHg or 20 mmHg in default value so that individual medical institutions can optionally select.

When one eye is measured a plurality of times, it is desirable that the setting of the still image be performed with respect to the first time measurement alone. This is because displaying each measurement reduces the examination efficiency and because the check of eyelashes can be made at the first time measurement. When attempting to clear the display of the still image, the display can be cleared by touching any switch or operation section, as described above. Besides, the display is automatically cleared after the expiration of a predetermined time interval.

As is evident from the foregoing, the noncontact tonometer according to the present invention is capable of showing the cause of an error to an examinee when a measured result was not obtained. Therefore, for example, when a fixation disparity of the subject's eye occurs, the examiner can urge the examinee to watch a fixation target at the next measurement. Similarly, when the eyelid of the examinee hangs down, the examiner can perform measurement by assisting the examinee regarding the eyelid during the next measurement. These adjustments allow the next measurement to be a reliable one.

Also, since the noncontact tonometer according to the present invention displays an error only when necessary, as compared with the conventional arts, it is possible to prevent the examination efficiency from being reduced. Moreover, the slow reproduction of moving images for a more detailed check is easy for the examiner to understand. Furthermore, when the measured value exceeds the standard intraocular pressure value, it can be checked whether the eyelashes of a subject eye have an influence on it.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A noncontact tonometer, comprising:
   blowing means for blowing air onto a cornea;
   photographing means for photographing an image of an anterior ocular segment;
   storage means for storing the image of the anterior ocular segment;
   control means for causing said storage means to store the image of the anterior ocular segment substantially immediately before air is blown onto the cornea;
   intraocular pressure measuring means for measuring an intraocular pressure value and obtaining a measured result based on the amount of deformation of the cornea due to the air blown onto the cornea;
   display means for displaying the stored image of the anterior ocular segment; and
   determining means for determining whether the stored image of the anterior ocular segment is displayed on said display means or not, based on the measured result obtained by said intraocular pressure measuring means.

2. The noncontact tonometer according to claim 1, wherein the stored image of the anterior ocular segment is displayed if the measured result is erroneous or exceeds a predetermined intraocular pressure value.

3. The noncontact tonometer according to claim 1, wherein said display means displays a target mark indicating a proper alignment position, together with the anterior ocular segment.

4. The noncontact tonometer according to claim 1, wherein said storage means records moving images, and wherein said display means reproduces the moving images at a slow speed.

5. The noncontact tonometer according to claim 1, wherein said display means displays the stored image of the anterior ocular segment on one portion of a display screen.

6. A noncontact tonometer, comprising:
   a nozzle for blowing air onto a cornea;
   an image pickup device for photographing an image of an anterior ocular segment;
   a memory for storing the image of the anterior ocular segment;
   a CPU for causing said memory to store the image of the anterior ocular segment substantially immediately before air is blown onto the cornea;
   an intraocular pressure sensor for measuring an intraocular pressure value and obtaining a measured result based on the amount of deformation of the cornea due to the air blown onto the cornea; and
   a display screen for displaying the stored image of the anterior ocular segment,
   wherein the CPU determines whether the stored image of the anterior ocular segment is displayed on said display means or not, based on the measured result obtained by said intraocular pressure sensor.

7. The noncontact tonometer according to claim 6, wherein the stored image of the anterior ocular segment is displayed if the measured result is erroneous or exceeds a predetermined intraocular pressure value.

8. The noncontact tonometer according to claim 6, wherein said display screen displays a target mark indicating a proper alignment position, together with the anterior ocular segment.

9. The noncontact tonometer according to claim 6, wherein the memory records moving images, and wherein the display screen reproduces the moving images at a slow speed.

10. The noncontact tonometer according to claim 6, wherein the display screen displays the stored image of the anterior ocular segment on one portion of the display screen.

* * * * *